United States Patent
Wegelin et al.

(10) Patent No.: US 9,984,553 B2
(45) Date of Patent: *May 29, 2018

(54) HYGIENE COMPLIANCE MODULE

(71) Applicant: GOJO Industries, Inc., Akron, OH (US)

(72) Inventors: Jackson W. Wegelin, Stow, OH (US); Matthew J. Archer, Aurora, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/494,718

(22) Filed: Apr. 24, 2017

(65) Prior Publication Data

US 2017/0229002 A1    Aug. 10, 2017

Related U.S. Application Data

(63) Continuation of application No. 15/138,760, filed on Apr. 26, 2016, now Pat. No. 9,633,544, and a continuation of application No. 15/139,641, filed on Apr. 27, 2016, now Pat. No. 9,633,545, and a continuation of application No. 15/137,487, filed on Apr. 25, 2016, now Pat. No. 9,633,543, said application No. 15/138,760 is a continuation of application No. 14/467,356, filed on Aug. 25, 2014, (Continued)

(51) Int. Cl.
*G08B 23/00* (2006.01)
*G08B 21/24* (2006.01)
*A47K 5/12* (2006.01)

(52) U.S. Cl.
CPC .......... *G08B 21/245* (2013.01); *A47K 5/1217* (2013.01)

(58) Field of Classification Search
CPC .............. G08B 21/245; G06K 7/10366; A47K 5/1202; A47F 1/03
USPC ........... 340/573.1, 539.1, 539.23, 572.1, 5.8, 340/13.24
See application file for complete search history.

(56) References Cited

U.S. PATENT DOCUMENTS 5,687,717 A    11/1997  Halpern et al.
5,945,910 A    8/1999   Gorra
(Continued)

FOREIGN PATENT DOCUMENTS

EP    2223642 A2    9/2010
JP    2002143022    5/2002
(Continued)

OTHER PUBLICATIONS

Third-Party Submission Under 37 CFR 1.290—Concise Description of Relevance; dated Dec. 27, 2016; 56 pages.
(Continued)

*Primary Examiner* — Phung Nguyen
(74) *Attorney, Agent, or Firm* — Calfee, Halter, Griswold LLP

(57) ABSTRACT

A hygiene compliance module is configured to be retrofit with a compatible dispenser to enable hygiene compliance monitoring functions. The hygiene compliance module is configured to be coupled to the dispenser via a communication interface to receive power, ground, and dispenser actuation signals therefrom. In addition, the hygiene compliance module is enabled to communicate with a wireless data tag that is worn by a user of the dispenser and with a remote hygiene compliance monitoring station.

20 Claims, 8 Drawing Sheets

Related U.S. Application Data now Pat. No. 9,349,274, said application No. 15/139,641 is a continuation of application No. 14/467,356, filed on Aug. 25, 2014, now Pat. No. 9,349,274, said application No. 15/137,487 is a continuation of application No. 14/467,356, filed on Aug. 25, 2014, now Pat. No. 9,349,274, which is a continuation of application No. 14/028,989, filed on Sep. 17, 2013, now Pat. No. 8,847,752, which is a continuation of application No. 12/941,287, filed on Nov. 8, 2010, now Pat. No. 8,558,701.

(56) References Cited

U.S. PATENT DOCUMENTS

| | | | |
|---|---|---|---|
| 6,893,321 B1 | 5/2005 | Buchanan et al. | |
| 6,977,588 B2 | 12/2005 | Scholz | |
| RE40,588 E | 11/2008 | Ostendorf et al. | |
| 8,085,155 B2 | 12/2011 | Prodanovich | |
| 8,427,323 B2 | 4/2013 | Alper | |
| 8,558,701 B2 | 10/2013 | Wegelin et al. | |
| 8,646,656 B2 | 2/2014 | Johnson | |
| 8,847,752 B2 | 9/2014 | Wegelin et al. | |
| 9,349,274 B2 | 5/2016 | Wegelin et al. | |
| 9,558,648 B2 | 1/2017 | Douglas | |
| 9,633,543 B2 | 4/2017 | Wegelin | |
| 9,633,545 B2 | 4/2017 | Wegelin | |
| 9,663,544 B2 | 4/2017 | Wegelin | |
| 2004/0090333 A1* | 5/2004 | Wildman | G06F 19/3418 340/573.1 |
| 2007/0135866 A1 | 6/2007 | Baker et al. | |
| 2008/0001763 A1* | 1/2008 | Raja | A61L 2/18 340/573.1 |
| 2008/0177155 A1 | 7/2008 | Hansen et al. | |
| 2009/0301523 A1 | 12/2009 | Barnhill | |
| 2010/0097224 A1 | 4/2010 | Prodanovich et al. | |
| 2010/0117836 A1 | 5/2010 | Seyed Momen | |
| 2010/0187251 A1 | 7/2010 | Simmons | |
| 2010/0188228 A1* | 7/2010 | Hyland | G08B 21/22 340/573.1 |
| 2010/0328076 A1* | 12/2010 | Kyle | G06F 19/327 340/573.1 |
| 2011/0169646 A1* | 7/2011 | Raichman | G08B 21/245 340/573.1 |
| 2011/0193703 A1 | 8/2011 | Payton et al. | |
| 2014/0015670 A1 | 1/2014 | Wegelin et al. | |

FOREIGN PATENT DOCUMENTS

| | | |
|---|---|---|
| JP | 200761157 | 3/2007 |
| JP | 2007525258 | 9/2007 |
| JP | 2010227560 | 10/2010 |
| WO | 02094073 A1 | 11/2001 |
| WO | 2005065509 | 7/2005 |
| WO | 2008088424 A1 | 7/2008 |
| WO | 2009134242 A1 | 11/2009 |

OTHER PUBLICATIONS

Third-Party Submission Under 37 CFR 1.290—Concise Description of Relevance; dated Dec. 27, 2016; 39 pages.
Patent Examination Report No. 1 from Australian Patent Application No. 2015258158 dated May 2, 2016.
Response to Patent Examination Report No. 1 from Australian Patent Application No. 2015258158 dated Aug. 19, 2016.
Notice of Reasons for Rejection from Japanese Patent Application No. 2013-538767 dated Apr. 20, 2016.
Office Action for U.S. Appl. No. 15/138,760 dated Aug. 22, 2016.
Office Action for U.S. Appl. No. 15/137,487 dated Aug. 19, 2016.
Office Action for U.S. Appl. No. 15/139,641 dated Sep. 9, 2016.
Office Action for Chinese Patent Application No. 201510755782.4 dated Jul. 24, 2017.
Office Action for Canadian Patent Application No. 2817080 dated Sep. 14, 2017.

* cited by examiner

HYGIENE COMPLIANCE MODULE

RELATED APPLICATIONS

This application is a continuation of U.S. patent application Ser. No. 15/139,641 filed on Apr. 27, 2016 and entitled HYGIENE COMPLIANCE MODULE, which will issue as U.S. Pat. No. 9,633,545; U.S. patent application Ser. No. 15/138,760 filed on Apr. 26, 2016 and entitled HYGIENE COMPLIANCE MODULE, which will issue as U.S. Pat. No. 9,633,544; and U.S. patent application Ser. No. 15/137,487 filed on Apr. 25, 2016 and entitled HYGIENE COMPLIANCE MODULE, which will issue as U.S. Pat. No. 9,633,543; which are continuations of U.S. patent application Ser. No. 14/467,356, now U.S. Pat. No. 9,349,274 filed on Aug. 25, 2014 and entitled HYGIENE COMPLIANCE MODULE; which is a continuation of U.S. patent application Ser. No. 14/028,989, now U.S. Pat. No. 8,847,752 filed on Sep. 17, 2013 and entitled HYGIENE COMPLIANCE MODULE; which is a continuation of U.S. patent application Ser. No. 12/941,287, now U.S. Pat. No. 8,558,701 filed on Nov. 8, 2010 and also entitled HYGIENE COMPLIANCE MODULE. All of which are incorporated herein by reference in their entirety.

TECHNICAL FIELD

The present invention generally relates to dispensers, such as soap dispensers. Particularly, the present invention relates to hygiene compliance modules that are capable of being retrofit with existing dispensers to enable hygiene compliance monitoring functions.

BACKGROUND OF THE INVENTION

Recently, the public has become increasingly concerned with disease and its transmission, and such, there is an increased awareness of the importance of cleansing and hygiene in general. For example, with respect to the transmission of E. coli in the food services industry, the rhinovirus in elementary schools, and nosocomial diseases within healthcare facilities, numerous studies have cited hand hygiene as an effective measure to guard against disease transmission. In response, the health care industry, the food services industry, and the hotel and travel industries have been forced to examine their protocols and procedures to ensure that their personnel are adopting hand sanitizing habits that are efficacious in the prevention of disease transmission.

In response, as an effort to provide sufficient opportunities for individuals to have access to soap and sanitizers, many institutions and industries have increased the number of installed dispensers to allow individuals to clean and sanitize their hands. And while the availability of soap and sanitizers has increased the opportunities for individuals to wash or sanitize their hands, there is still a lack of compliance with predetermined hand washing hygiene standards. Furthermore, in order to minimize the potential transmission of bacteria or viruses by hand washing, full compliance with hygiene standards must be observed, as the failure of one individual to properly sanitize his or her hands can negate the efforts of others who come in contact with such individuals.

In order to achieve the desired level of hygiene compliance, many institutions have employed hygiene compliance monitoring systems that include dispensers that are capable of tracking the usage of the dispenser for identified individuals. Unfortunately, for entities with a large number of existing dispensers already installed, which lack hygiene compliance monitoring functionality, it would require the complete replacement of those dispensers with new dispensers that have hygiene compliance features, which is costly, and in many circumstances unfeasible.

Therefore, there is a need for a hygiene compliance module that can be retrofit with previously installed dispensers to provide hygiene compliance monitoring features. In addition, there is a need for a hygiene compliance module that can be retrofit in a user-friendly manner with an existing dispenser to provide hygiene compliance monitoring functionality. Furthermore, there is a need for a hygiene compliance module that can be retrofit with previously installed dispensers and that is powered by the power source provided by the dispenser to which it is attached. There is also a need for a hygiene compliance module that when retrofit with a previously installed dispenser is enabled or disabled depending on whether the hygiene compliance module has been authenticated by the dispenser.

SUMMARY OF THE INVENTION

In light of the foregoing, it is a first aspect of the present invention to provide a hygiene compliance module for a dispenser having a dispenser controller that supplies an actuation signal to a communication interface when an actuator is engaged to dispense material, the hygiene compliance module comprising a card adapted to be coupled to the communication interface of the dispenser; a module controller disposed on said card, said module controller configured to detect the actuation signal as dispensing event data; and a transmitter and receiver coupled to said module controller, said receiver configured to wirelessly receive an identification code from a wireless data tag, wherein when the actuator of the dispenser is engaged, said module controller associates said identification code of said data tag with said dispensing event data and transmits said code and said dispensing event data via said transmitter to a hygiene compliance monitoring station.

It is another aspect of the present invention to provide a method of enabling hygiene compliance monitoring functionality at a dispenser comprising providing a dispenser having a communication interface having an actuation terminal, coupling a hygiene compliance module to said communication interface, providing a data tag that wirelessly transmits an identification code to said hygiene compliance module, monitoring said actuation terminal at said hygiene compliance module, dispensing material from said dispenser, detecting an actuation signal on said actuation terminal at said hygiene compliance module as dispensing event data, and associating said identification code with said dispensing event data.

Yet another aspect of the present invention is to provide a hygiene compliance module for a dispenser having a dispenser controller that supplies an actuation signal to a communication interface when an actuator is engaged to dispense material, the hygiene compliance module comprising a card adapted to be coupled to the communication interface of the dispenser; a module controller disposed on said card, said module controller configured to detect the actuation signal as dispensing event data; and a transmitter coupled to said module controller, wherein when the dispenser actuator is engaged, said module controller transmits said dispensing event data via said transmitter to a monitoring station.

It is a further aspect of the present invention to provide a hygiene compliance module having a communication interface that is configured in accordance with a configuration code, and a dispenser controller providing an actuation signal to the communication interface when an actuator is engaged to dispense material, the hygiene compliance module comprising a card adapted to be coupled to the communication interface of the dispenser; a module controller disposed on said card, said module controller configured to be modified in accordance with said configuration code to compatibly communicate with the dispenser through the communication interface; and a transmitter coupled to said module controller, wherein when the dispenser actuator is engaged said module controller detects the actuation signal as dispensing event data, and said module controller transmits said dispensing event data via said transmitter to a monitoring station.

BRIEF DESCRIPTION OF THE DRAWINGS

These and other features and advantages of the present invention will become better understood with regard to the following description, appended claims, and accompanying drawings where:

BEST MODE FOR CARRYING OUT THE INVENTION

Figure 1:
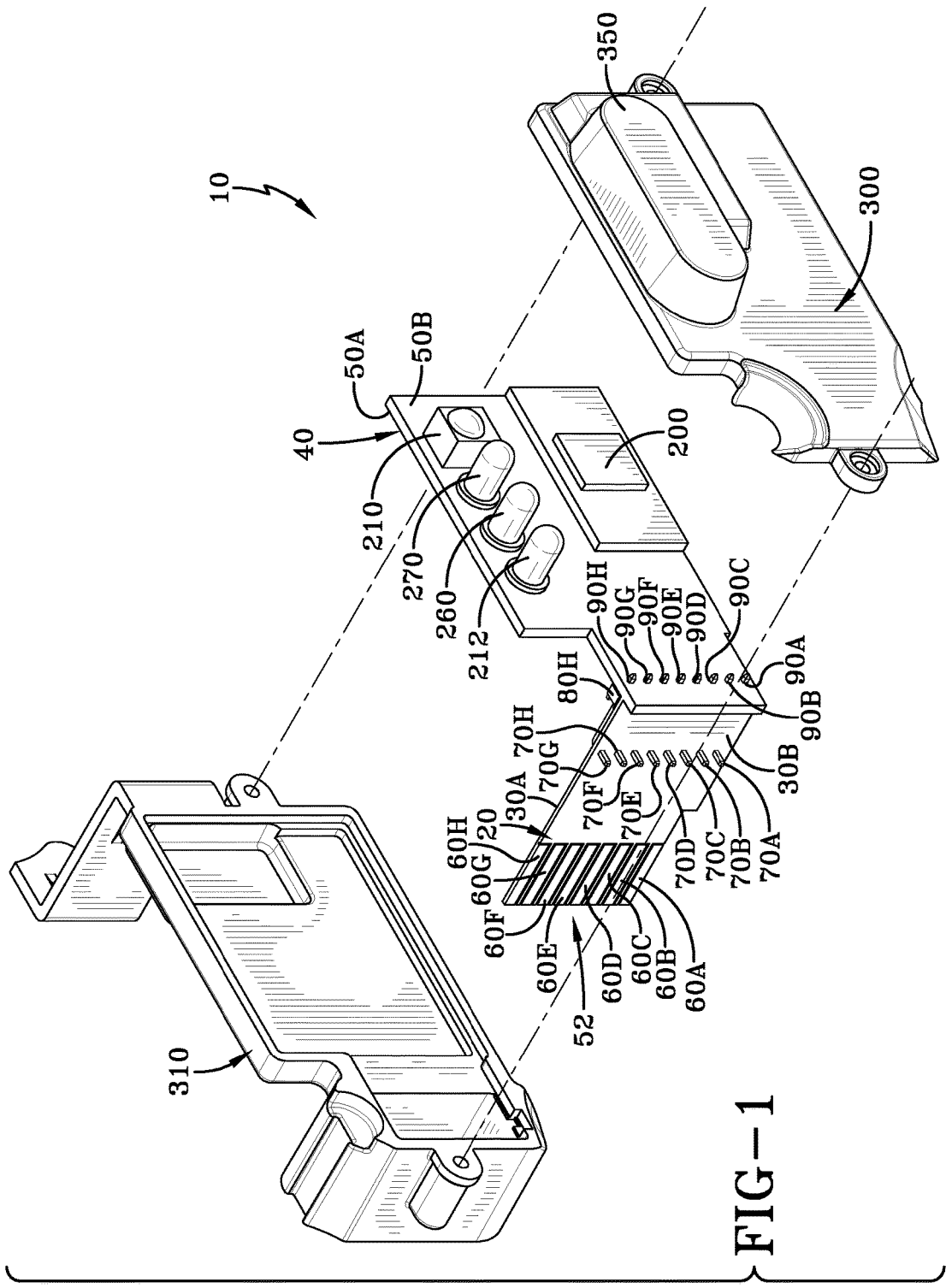
FIG. 1 is an exploded perspective view of a hygiene compliance module in accordance with the concepts of the present invention.
Figure 2:
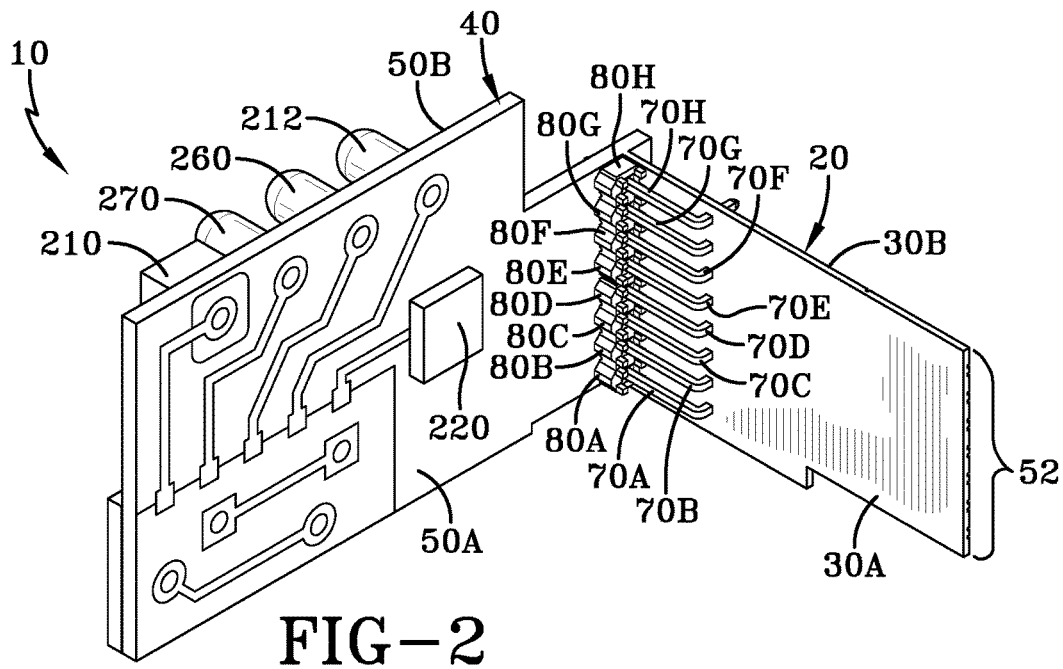
FIG. 2 is a perspective view of the rear portion of the hygiene compliance module in accordance with the concepts of the present invention.
Figure 3:
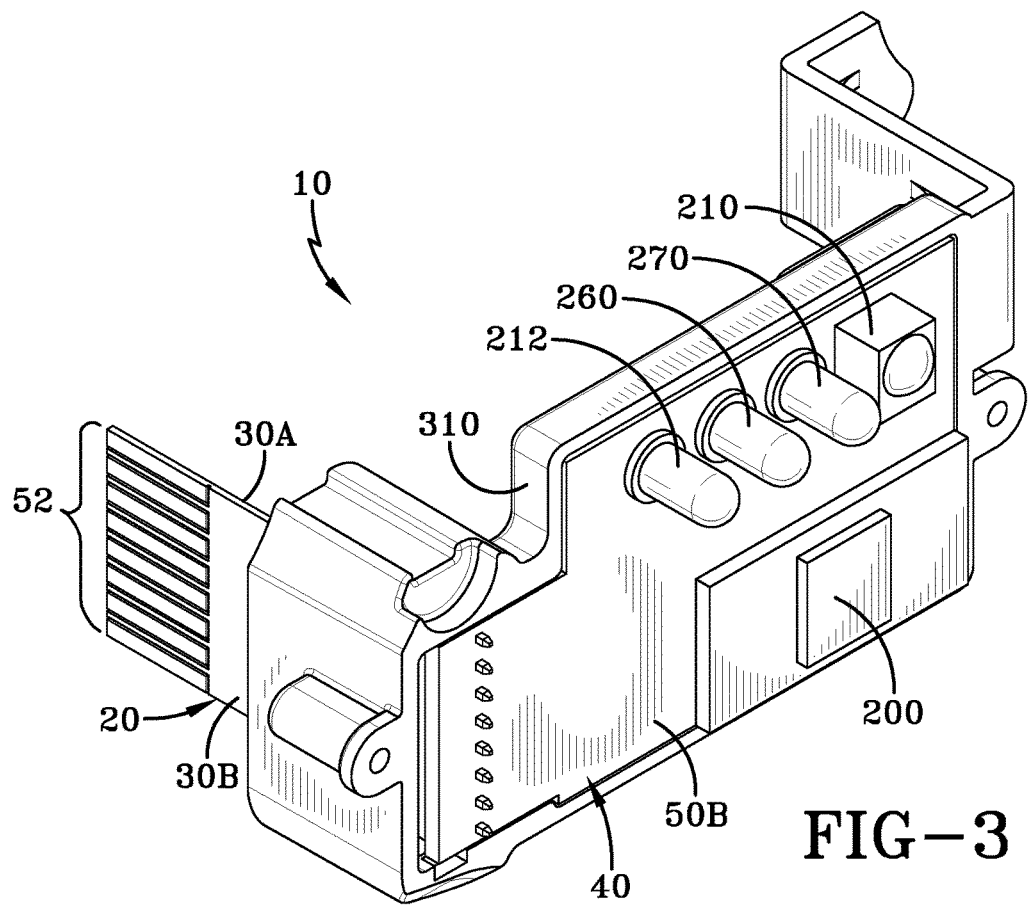
FIG. 3 is a perspective view of the hygiene compliance module with its rear cover attached and its front cover removed in accordance with the concepts of the present invention.
Figure 4:
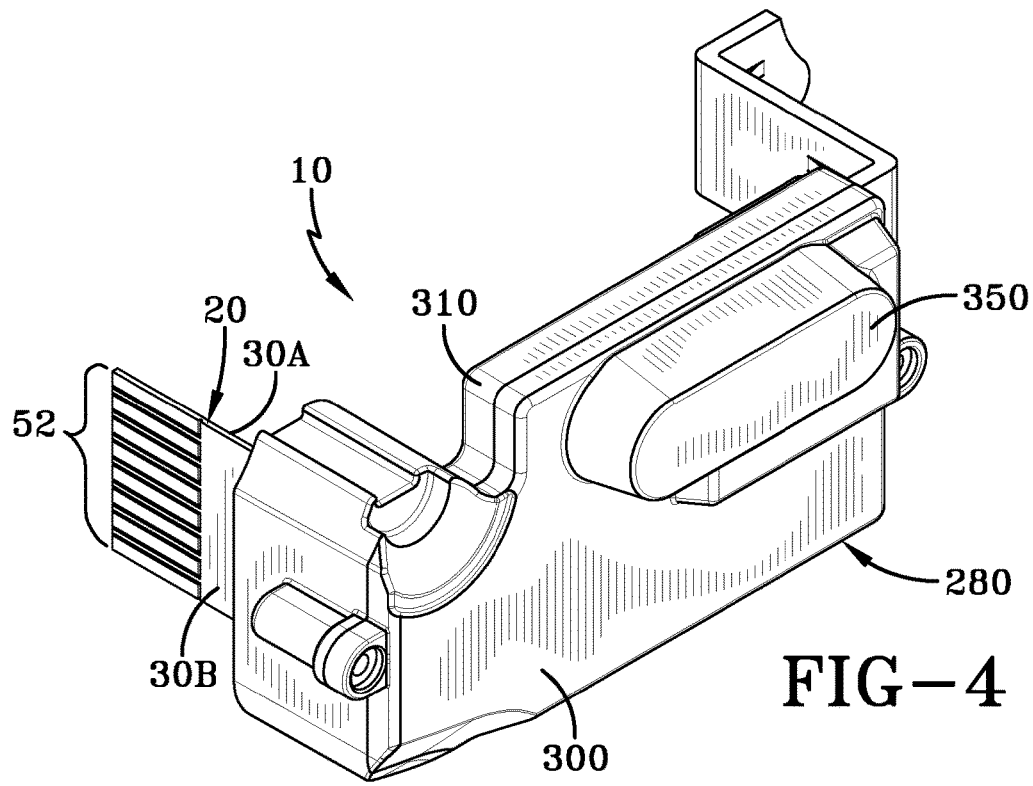
FIG. 4 is a perspective view of the hygiene compliance module having its front and rear covers attached thereto in accordance with the concepts of the present invention.
Figure 5:
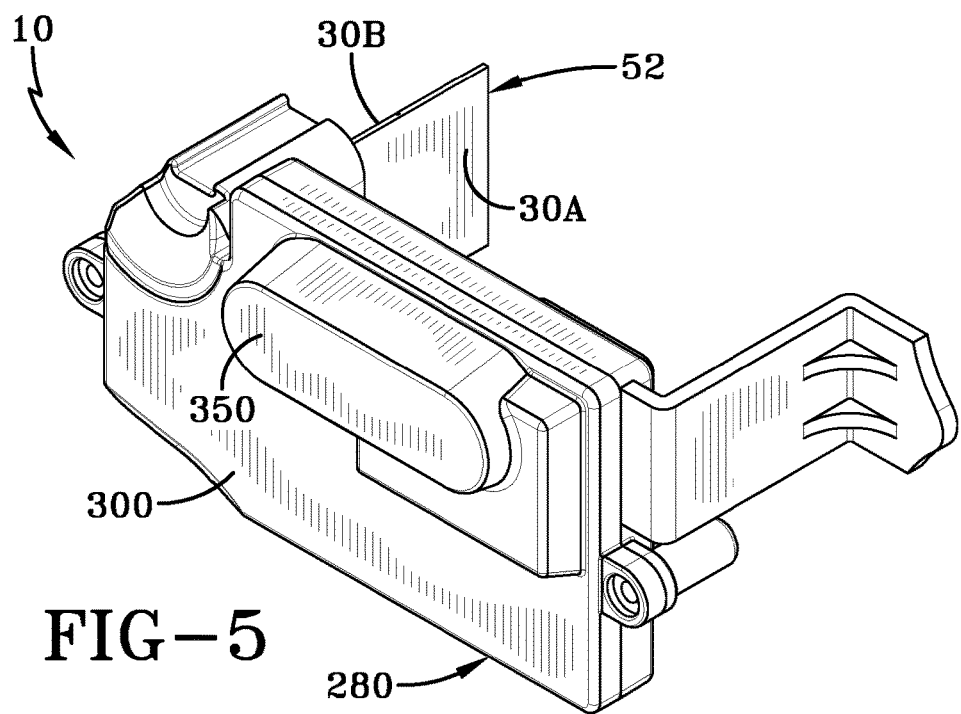
FIG. 5 is another perspective view of the hygiene compliance module having its front and rear covers attached thereto in accordance with the concepts of the present invention.
Figure 6:
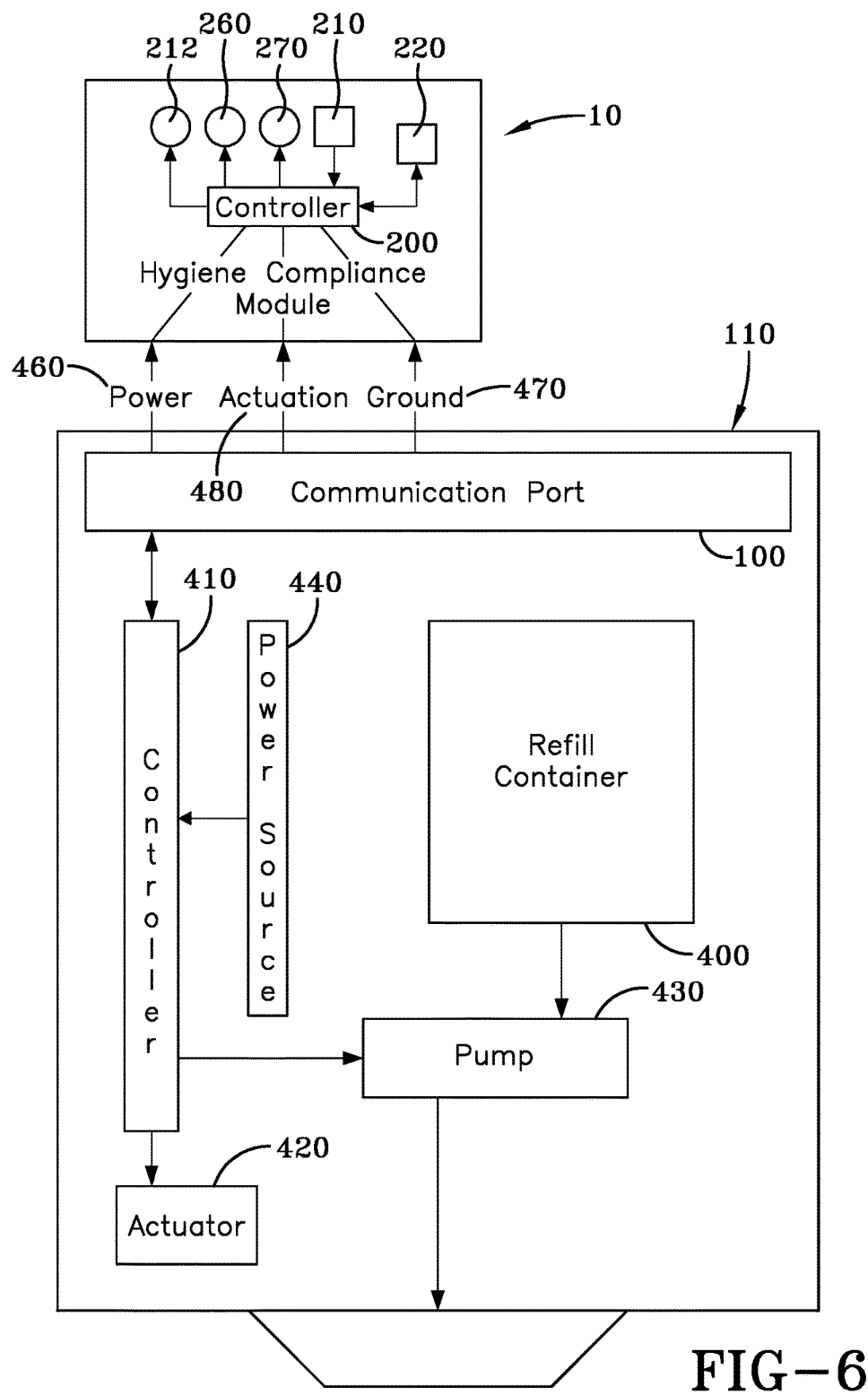
FIG. 6 is a schematic view of the dispenser compatible for use with the hygiene compliance module in accordance with the concepts of the present invention.
Figure 7:
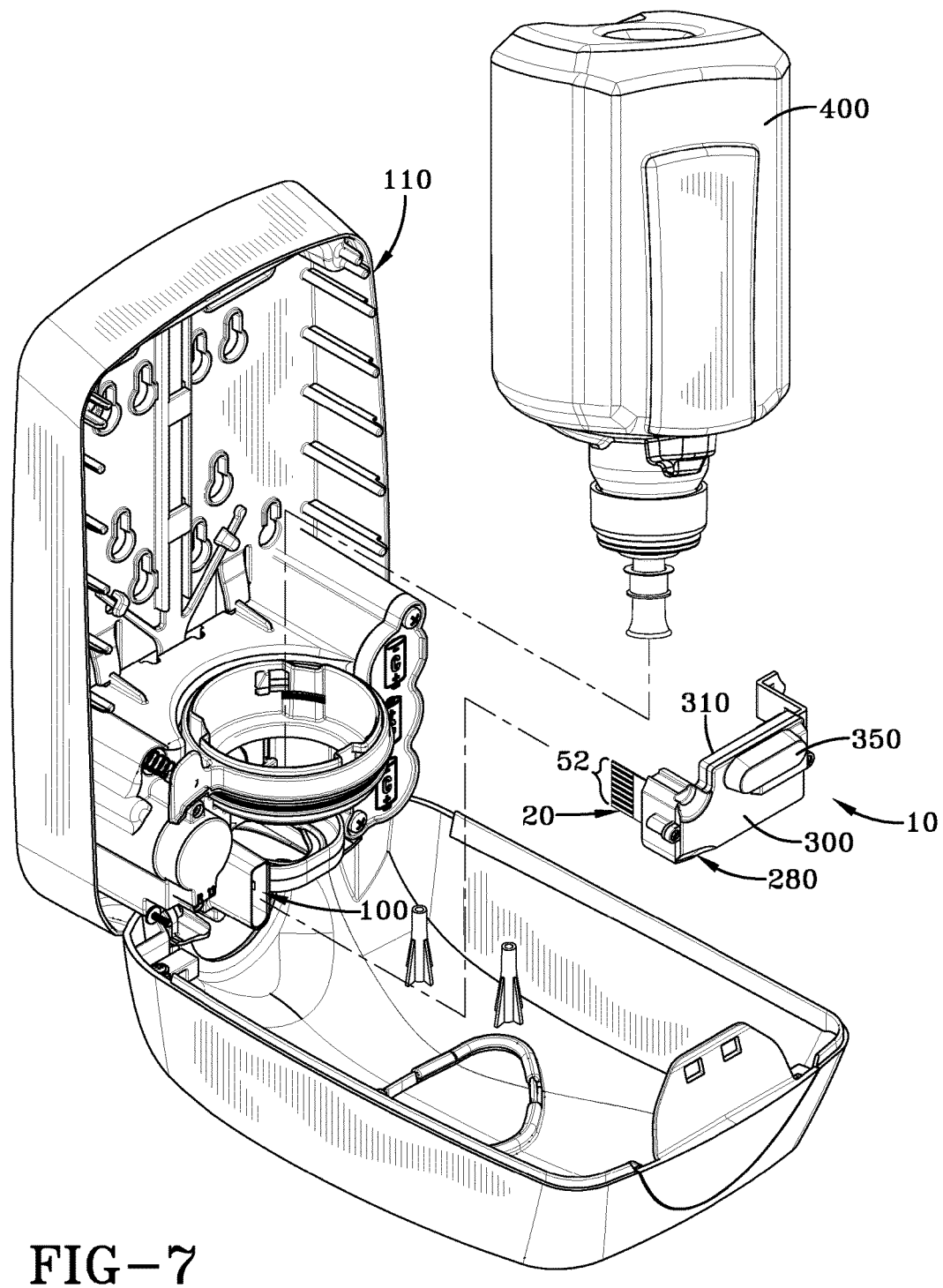
FIG. 7 is a perspective view of a dispenser configured to be retrofit with the hygiene compliance module in accordance with the concepts of the present invention.
Figure 8:
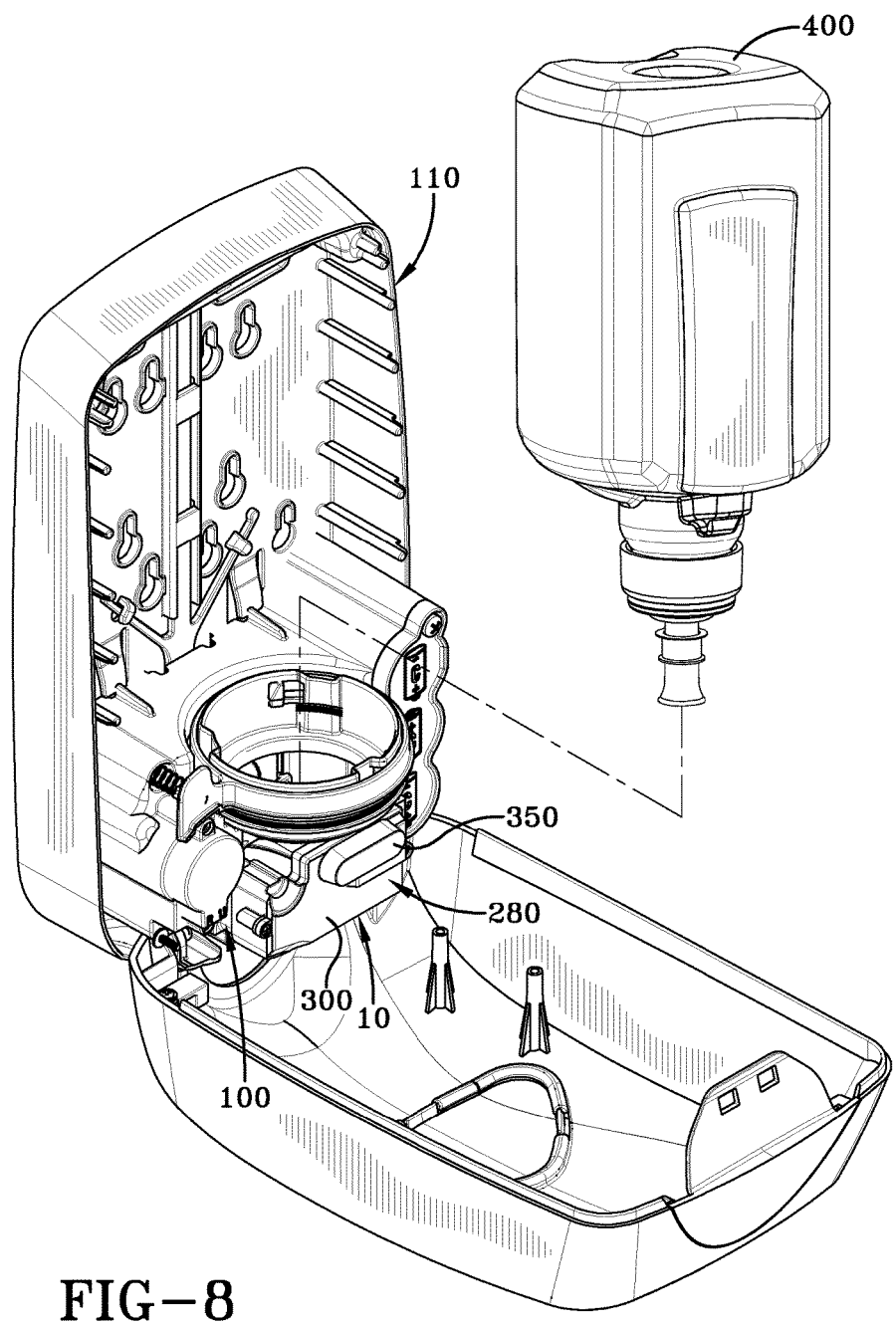
FIG. 8 is a perspective view of the dispenser having the hygiene compliance module attached thereto in accordance with the concepts of the present invention.
Figure 9A:
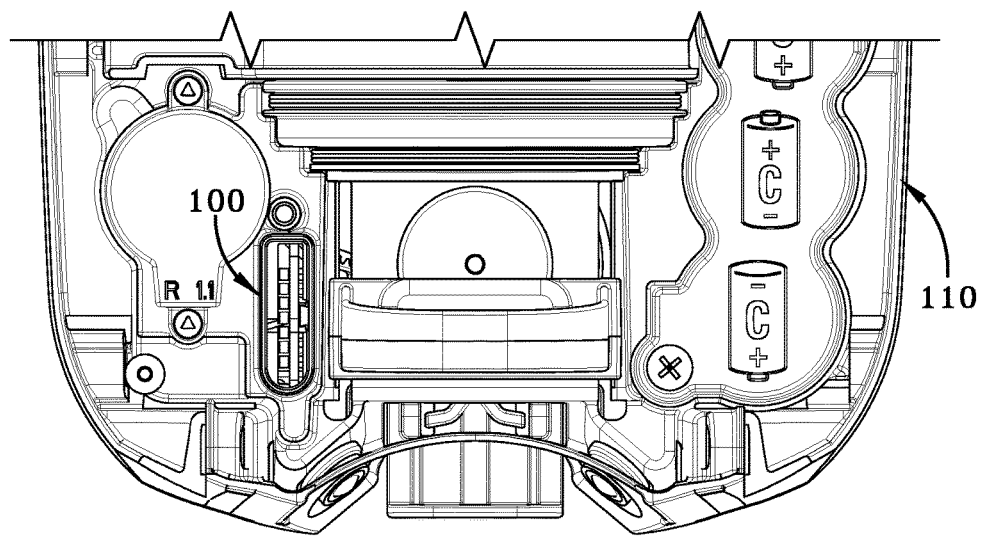
FIG. 9A is an elevational view of the dispenser showing a communication interface to enable the retrofit connection of the hygiene compliance module in accordance with the concepts of the present invention.
Figure 9B:
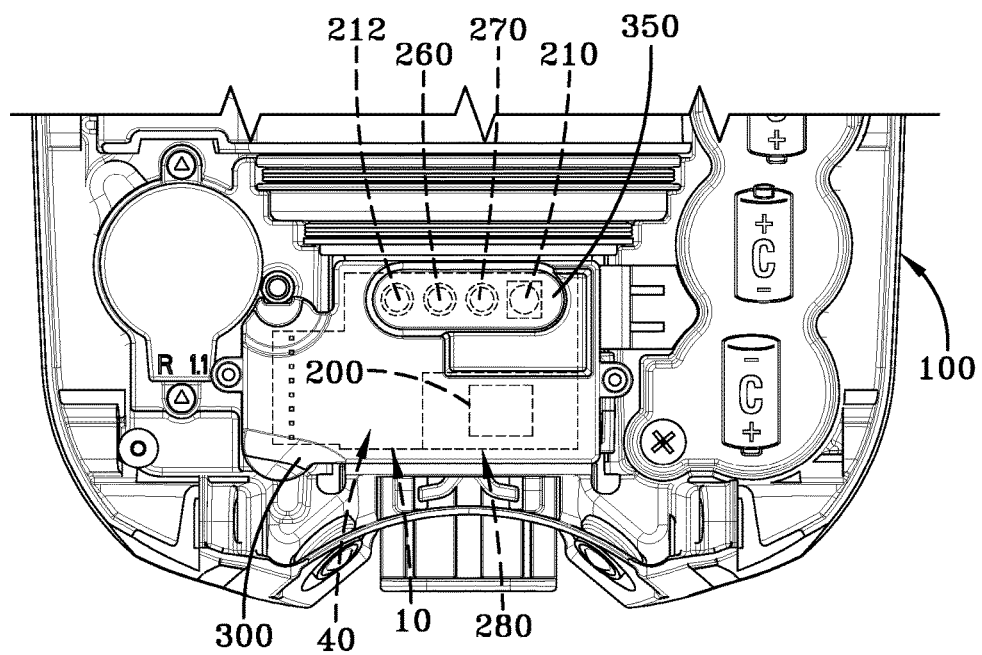
FIG. 9B is an elevational view of the dispenser showing the hygiene compliance module coupled to the communication interface of the dispenser in accordance with the concepts of the present invention.

A hygiene compliance module is generally referred to by the numeral 10, as shown in FIGS. 1-6 of the drawings. The hygiene compliance module 10 comprises a riser card 20 having opposed inner and outer surfaces 30A and 30B, and a main card 40 that has opposed inner and outer surfaces 50A and 50B. The riser card 20 and the main card 40, which comprises a circuit board, are coupled together in a manner to be discussed. It should be appreciated, however, that the riser and main cards 20,40 may be made integral to form a single, unified, card structure. The riser card 20 includes an edge connector 52 comprising a plurality of electrical contacts 60A-H that are respectively coupled to pins 70A-H. The pins 70A-H extend through the riser card 20 and extend at a substantially right angle, so as to be substantially parallel to the inner surface 30A of the riser card 20, where the pins 70A-H are terminated at respective connection blocks 80A-H provided by the main card 40. The connection blocks 80A-H support respective pins 60A-H and allow them to extend into corresponding contact apertures 90A-H that are provided by the main card 40. As such, the contact apertures 90A-H electrically couple the edge connector 52 contacts 60A-H to various electrical components provided by the hygiene compliance module 10 to be discussed. Specifically, the edge connector 52 of the riser card 20 is configured to connect to a communication interface 100, such as a communication port, so as to access the power, ground, and actuation signals provided by a dispenser 110, such as a soap dispenser shown in FIG. 6, to enable various hygiene compliance monitoring functions provided by the module 10 to be discussed. In one aspect, the contacts 60A, 60G, and 60H are configured to receive respective ground, power, and actuation signals that are provided by the communication interface 100.

Figure 10:
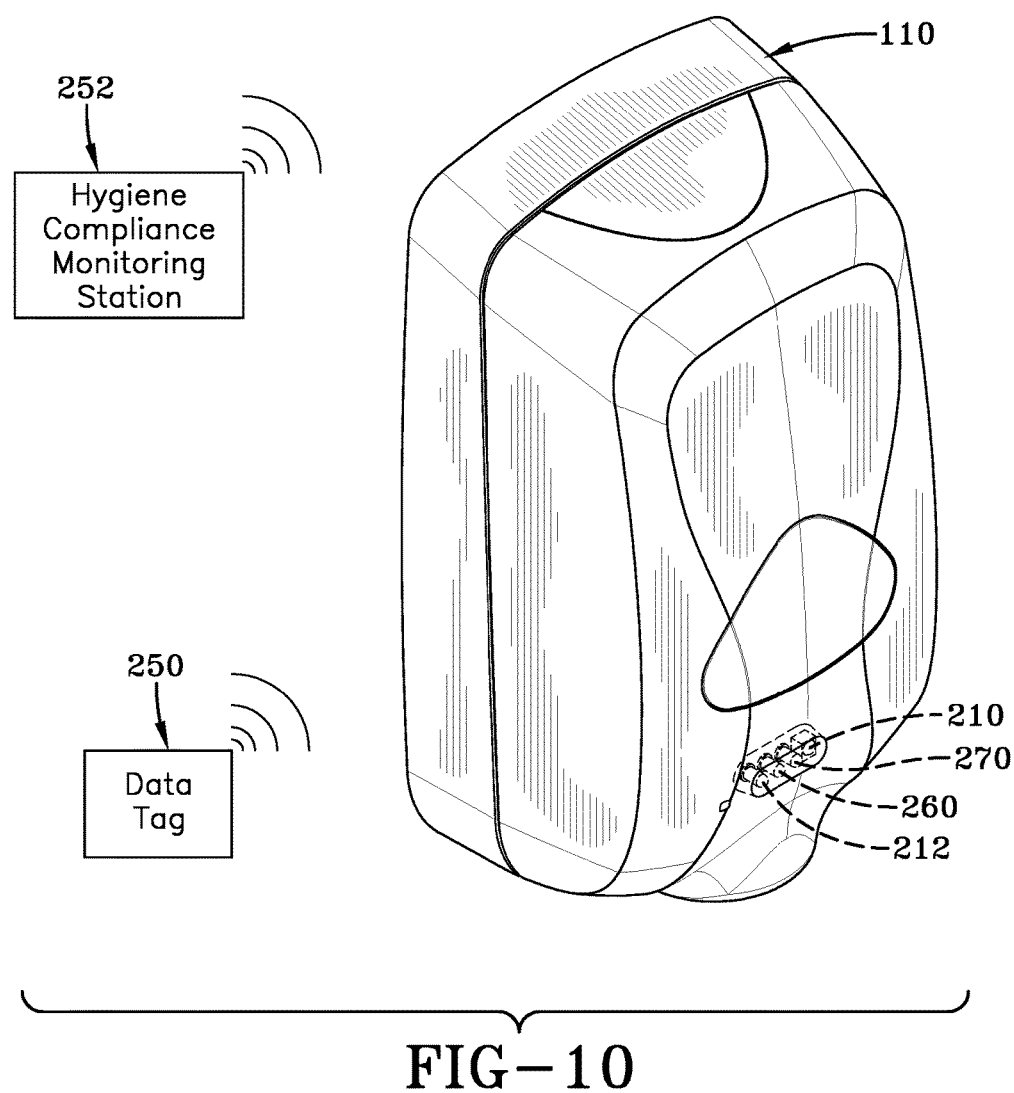
FIG. 10 is a perspective view of the dispenser that allows the retrofit hygiene compliance module to wirelessly communicate data therethrough in accordance with the concepts of the present invention.

Disposed on the outer surface 50B of the main card 40 is a module controller 200 that is configured with the necessary hardware, software, and/or memory that is needed to carry out the functions to be discussed. In addition to being coupled to the contacts 60A-H of the edge connector 52, the module controller 200 is coupled to an IR (infrared) receiver 210, an IR (infrared) transmitter 212, and to a RF (radio frequency) transceiver 220. As such, the IR receiver 210 and the RF transceiver 220 are configured to wirelessly communicate with a data tag 250, such as an RFID (radio frequency identification) tag, that is worn by an individual, and a remote hygiene compliance monitoring station 252, as shown in FIG. 10. The data tag 250 and the monitoring station 252 may be configured to transmit and/or receive IR or RF signals that are compatible with the operation of the compliance module 10. In addition, the hygiene compliance monitoring station 252 may comprise any suitable computing system that is configured to acquire and organize the hygiene compliance data that is wirelessly transferred from the compliance module 10. Alternatively, the hygiene compliance monitoring station 252 may be configured to transmit setting data to the compliance module 10 and/or dispenser 110 to change or otherwise modify one or more of their operating parameters. Moreover, it also contemplated that the compliance module 10 may communicate with the data tag 250 and the monitoring station 252 using only RF signals, only IR signals or any combination thereof, and as such, only the particular IR or RF transmitters and receivers necessary for transmitting and receiving the particular communication signals needed to carry out the functions discussed herein are provided by the compliance module 10. In one aspect, it should be appreciated that the RF transceiver 220 may be configured as an RF transmitter only.

The main card 40 also includes a pair of visual indicators 260 and 270, which comprises LEDs (light emitting diodes) or any other suitable indication means, including an audible indication means, such as a tone generator. Specifically, the indicator 260 provides a visual or audible prompt to identify when the data tag 250 is recognized or authenticated by the module controller 200, while indicator 270 provides a visual prompt to identify when the dispenser 110 has dispensed material to an individual wearing the data tag 250.

The hygiene compliance module 10 includes a protective housing 280 that is comprised of front and rear covers 300 and 310, as shown in FIGS. 1 and 3-5, which serve to enclose the main card 40 and a portion of the riser card 20. The front cover 300 includes a transparent, or at least partially transparent, viewing window 350 that allows an individual to view the indicators 260 and 270. In addition, the viewing window 350 is also configured to be electrically transparent to the passage of wireless IR (infrared) and RF (radio frequency) signals that are communicated to and from the hygiene compliance module 10. The front and rear covers 300 and 310 are retained together using any suitable means of fixation, including screws or adhesive for example. It should be appreciated that the protective housing 280 may be formed from any suitable material, such as plastic for example.

The hygiene compliance module 10 is configured to be retrofit with the dispenser 110, as shown in FIGS. 6-10, which may include a soap, sanitizer, or moisturizer dispenser for example, although the dispenser 110 may be configured to dispense any suitable material. The dispenser 110 is configured to dispense liquid material from a replaceable refill container 400 that is removably attached to the dispenser 110. The refill container 400 may contain any desired material, such as soap, sanitizer, or moisturizer for example. The dispenser 110 includes a controller 410 that provides the necessary hardware and/or software needed to carry out the functions to be discussed. The controller 410 is coupled to an actuator 420, which may comprise a biometric sensor or proximity sensor that is capable of automatically detecting the presence of an individual's hands. The actuator 420 may also comprise a mechanical switch or button that is configured to be manually depressed by an individual. The dispenser 110 also includes a pump 430 that is coupled to the controller 410, which is controlled to dispense a predetermined amount of liquid material from the refill container 400 that is fluidly coupled thereto when the actuator 420 is engaged. For example, in the case where the actuator 420 comprises a proximity sensor, the controller 410 causes the pump 430 to dispense an amount of liquid material from the refill container 400 when the actuator 420 detects the presence of the individual's hands. The dispenser 110 is powered by a power source 440, such as a battery, or may be powered by any other suitable power source, such as a solar cell or A.C. (alternating current) mains power provided by an electrical outlet.

To facilitate the retrofitting of the hygiene compliance module 10 with the dispenser 110 the communication interface 100 is utilized. Specifically, the communication interface 100 is coupled to the controller 410 of the dispenser 110 and, as such, provides an electrical interface for accessing power, ground, and actuation terminals 460, 470, and 480 that provide corresponding signals thereon generated from the controller 410 during the operation of the dispenser 110. As such, when the edge connector 52 of the module 10 is inserted into the communication interface 100, the contacts 60A, 60G, and 60H couple ground, power and actuation signals supplied by respective terminals 460, 470, 480 to the module controller 200 of the hygiene compliance module 10. It should also be appreciated that contacts 60B-F are utilized by the controller 200 of the hygiene compliance module 10 for authentication purposes to ensure that the dispense controller 410 communicates only with authorized compliance modules 10 for which the dispenser 110 and compliance module 10 have been configured. Such a system, discussed in further detail below, prevents unauthorized compliance modules 10 or any other electric device inserted into the communication interface 100 from communicating with the dispense controller 410.

With the basic operation of the dispenser 110 set forth, the following discussion will now present the manner in which the hygiene compliance module 10 is retrofit with the dispenser 110. Specifically, the compliance module 10 is interfaced or otherwise plugged into the dispenser 110, such that the edge connector 52, having electrical contacts 60A-H, is received within the communication interface 100, as shown in FIGS. 7-10, allowing the module 10 to be in electrical communication with the controller 410. Once the compliance module 10 is coupled to the communication interface 100 of the dispenser 110, the compliance module 10 is able to access the power, ground, and actuation signals provided by corresponding terminals 460, 470, 480 of the dispenser 110. In particular, the hygiene compliance module 10 is powered by the power and ground signals provided on terminals 460, 480 of the communication interface 100 that are coupled to the power source 440 and the controller 410 of the dispenser 110. Additionally, the actuation signal provided on terminal 470 of the communication interface 100, which is generated by the dispenser controller 410 to actuate the pump 430 to dispense material when the actuator 420 is engaged, is processed by the module 10 and used to carry out various hygiene compliance monitoring functions to be discussed. It should also be appreciated that in lieu of the use of a separate actuation signal (and contact 60H) that is generated by the dispenser controller 410 when a dispensing event occurs, the dispenser controller 410 may be configured to selectively supply power to the hygiene compliance module 10 to indicate when a dispensing event occurs. As such, the compliance module 10 would be powered and made operational to carry out the functions discussed herein each time a dispensing event takes place.

The hygiene compliance module 10 is configured to collect and share hygiene compliance data through wireless communication with the wireless data tag 250, such as an RFID (radio frequency identification) tag or other communication device, and the remote hygiene compliance station 252. In particular, the wireless data tag 250 is configured to be worn by an individual, such as a healthcare giver, who is engaging with the dispenser 110 to dispense an amount of material on his or her hands. When the individual wearing the data tag 250 engages the actuator 420 provided by the dispenser 110 to dispense material therefrom, the dispenser controller 410 generates an actuation signal. The actuation signal is used to actuate the pump 430 to complete the dispensing of material, and is also carried by the terminal 480 of the communication interface 100 to the module controller 200 of the hygiene compliance module 10. The receipt of the actuation signal via the communication interface 100 indicates to the compliance module 10 that a dispensing event in which an individual has dispensed material from the refill container 400 has occurred. Once the actuation signal is received by the compliance module controller 200, the unique identification code associated with each data tag 250 is wirelessly acquired via the IR receiver 210 (in the case of an IR transmitting data tag 250) or RF transceiver 220 (in the case of an RF transmitting data tag 250) and combined or otherwise associated with dispensing event data indicating that a dispensing event occurred before it is wirelessly communicated via the IR transmitter 212 or RF transceiver 220 as hygiene compliance data to the remote hygiene compliance monitoring station 252. Alternatively, the compliance module 10 may be configured to collect hygiene compliance data in an anonymous manner, such that the compliance module 10 does not associate the identification code of the data tag 250 with dispensing event data.

Moreover, the compliance module 10 may be configured to communicate with the data tag 250 in a 1-way manner in which the compliance module 10 only receives data, such as an identification code, from the data tag 250 or in a 2-way manner in which the compliance module 10 receives data from the data tag 250 and transmits data to the data tag 250. Similarly, the compliance module 10 may be configured to communicate with the monitoring station 252 in a 1-way manner in which the compliance module 10 only transmits compliance data to the monitoring station 252 or in a 2-way manner in which the compliance module 10 transmits hygiene compliance data to the monitoring station 252 and receives data, such as operation setting data associated with the modification of functions provided by the module 10, from the monitoring station 252. For example, the compliance module 10 may be configured with only the IR receiver 210 and an RF transmitter, such that the compliance module 10 receives data from the data tag 250 via the IR receiver 210, and forwards the data to the compliance monitoring station 252 using the RF transmitter.

In addition, the indicators 260 and 270 are respectively configured to indicate when the compliance module 10 has authenticated the data tag 250 as being authorized to access and use the dispenser 110, and when the dispenser 110 has completed a dispensing event. In one aspect, the hygiene compliance module 10 may acquire the unique identification code associated with the data tag 250 and wirelessly transmit it to the remote hygiene compliance monitoring station 252 for authentication before the operation of the dispenser 110 is enabled. If the remote hygiene compliance monitoring station 252 authenticates the data tag 250 identification code as being authorized, then it wirelessly transmits an authorization code to the hygiene compliance module 10 that enables the operation of the dispenser 110 for a limited period of time to allow the individual to dispense material from the dispenser 110.

Furthermore, the contacts 60B-F of the compliance module 10 may be selectively connected to the power terminal 470 and the ground terminal 460 of the dispenser 100. This allows the compliance module controller 200 to generate a code, such as a 5-bit authentication code, that is received by the dispenser controller 410. The dispenser controller 410 evaluates the authentication code against codes stored at the dispenser controller 410 or at the compliance monitoring station 252 to determine whether the code is valid or not. If the dispenser code 410 determines that the code is valid, the dispenser 110 and the compliance module 10 will continue to remain operable. However, if the dispenser 110 determines that the code is invalid, then the module 10 and/or dispenser 100 may be either fully or partially disabled. For example, in the case of an invalid code, the dispenser 110 may be partially disabled, such that the hygiene compliance module 10 interfaced therewith will not be recognized by the dispenser 100 or the functions provided by the compliance module 10 may be limited. Thus, in the event that an unauthorized device is coupled to the interface 100, which fails to generate a valid code, the device and/or dispenser 10 is fully or partially disabled. Such a system is beneficial in that it prevents unauthorized compliance modules 10 from being used with the dispenser 110.

In another aspect, the dispenser controller 410 may be configured to generate a configuration code, such as a 5-bit code, that is supplied through the interface 100 and received via contacts 60B-F coupled to the module controller 200 of the compliance module 10. The configuration code identifies the specific communication configuration that is to be utilized by the dispenser controller 410 during the communication between the dispenser 110 and the compliance module 10. As such, the module controller 200 must be able to interpret the meaning of the configuration code, and also be able to physically configure its internal components, such as the communication port coupled to contacts 60B-F, so that the specific contacts 60B-F identified by the configuration code are used in the specific manner defined in the configuration code in order for compatible communication with the dispenser controller 410 to occur. Thus, if the module controller 200 does not identify the correct contacts 60B-F to be used, and the correct function assigned to each contact 60B-F that is required for compatible communication to occur with the dispenser 110 from the configuration code received from the dispenser 110, then the compliance module 10 will be unable to provide hygiene compliance functions to the dispenser 110. In addition, the configuration code supplied by the dispenser 110 may be changed periodically by the dispenser 10 at predetermined or random intervals, or may be changed each time data or electronic signals are sent to the compliance monitor 10. Moreover, by requiring the hardware components (contacts 60B-F) of the compliance module 10 to be configured or utilized in a specific manner an added level of security is provided to further prevent unauthorized compliance modules from being interfaced with the dispenser 110.

It will, therefore, be appreciated that one advantage of the present invention is that a hygiene compliance module is configured to be retrofit with an installed dispenser to provide hygiene compliance monitoring functionality. Another advantage of the present invention is that the hygiene compliance module can utilize the power source of a dispenser when retrofit thereto. Yet another advantage of the present invention is that the hygiene compliance module can utilize the actuation signal of the dispenser in order to provide hygiene compliance monitoring functions when retrofit thereto. Still another advantage of the present invention is that if an authorized hygiene compliance module is interfaced with a dispenser, the dispenser and/or hygiene compliance module may be fully or partially disabled.

Although the present invention has been described in considerable detail with reference to certain embodiments, other embodiments are possible. Therefore, the spirit and scope of the appended claims should not be limited to the description of the embodiments contained herein.

What is claimed is:
1. A soap or sanitizer dispenser comprising:
a dispenser housing;
the dispenser housing having a base and a cover;
an actuator located within the dispenser housing;
a refill unit located within the dispenser housing;
   the refill unit including a container, a pump, and a soap or sanitizer;
a power source located in the dispenser housing;
a female connector located within the dispenser housing;
a power conductor for providing power from the power source to the female connector;
a dispenser controller;

a signal conductor for providing a signal indicative of a dispenser actuation to female connector; and
a compliance module;
the compliance module having
a circuit board;
a processor located on the circuit board;
a radio frequency transceiver located on the circuit board;
a housing at least partially surrounding the circuit board; and
a male connector for releasably connecting to the female connector for providing power to the processor and for providing the signal indicative of the dispenser actuation to the processor; and
wherein the radio frequency transceiver is configured to transmit a signal indicative of the dispenser actuation and to receive wireless communications from a data tag.

2. The soap or sanitizer dispenser of claim 1 wherein the module housing includes an opening, and wherein the male connector extends at least partially through the opening.

3. The soap or sanitizer dispenser of claim 1 further comprising an indicator light for indicating when soap or sanitizer is dispensed to an individual associated with the data tag.

4. The soap or sanitizer dispenser of claim 1 wherein the male connector has eight connection points.

5. The soap or sanitizer dispenser of claim 1 wherein the male connector more than three connection points.

6. The soap or sanitizer dispenser of claim 1 wherein the power source is a plurality of batteries and the plurality of batteries are located on a first side of the dispenser and the female connector is located on a second side of the dispenser.

7. The soap or sanitizer dispenser of claim 1 wherein the radio frequency transceiver receives a signal from the data tag that identifies the data tag.

8. The soap or sanitizer dispenser of claim 7 wherein the radio frequency transceiver transmits a signal that identifies the data tag.

9. The soap or sanitizer dispenser of claim 1 wherein the radio frequency transceiver transmits a signal indicative of a dispenser actuation to the data tag.

10. The soap or sanitizer dispenser of claim 1 wherein the radio frequency transceiver transmits a signal indicative of a dispenser actuation to a monitoring station.

11. A compliance module comprising:
a circuit board;
a housing surrounding the circuit board;
a controller located on the circuit board;
wireless communication circuitry located on the circuit board;
the wireless communication circuitry configured for receiving signals from a data tag and transmit one or more signals indicative of a dispenser actuation;
a connector extending at least partially through a hole in the housing,
a power conductor extending from the connector to the circuit board for providing power to at least one of the processor and the wireless communication circuitry; and a signal conductor extending from the connector to the circuit board for receiving a signal indicative of the dispenser actuation and providing that signal to the processor.

12. The compliance module of claim 11 wherein the circuit board is entirely enclosed within the housing.

13. The compliance module of claim 11 wherein the housing comprises a front cover and a rear cover.

14. The compliance monitoring system of claim 11 wherein the wireless communication circuitry comprises one or more radio frequency transceivers.

15. The compliance module of claim 11 further comprising an indicator to indicate when soap or sanitizer has been dispensed to an individual associated with the data tag.

16. A compliance monitoring system comprising:
a dispenser for dispensing soap or sanitizer;
the dispenser having
a dispenser controller that controls the operation of the dispenser;
one or more batteries that provide power to the controller and a compliance module;
a first connector;
a power conductor providing power to the first connector;
a signal conductor for providing a signal indicative of an actuation of the dispenser to the first connector;
a compliance module,
the compliance module having
a circuit board;
a module controller located on the circuit board;
a module housing surrounding the circuit board;
the module housing having a front cover and a rear cover;
module communication circuitry for wirelessly communicating with at least one of a compliance monitoring station and a data tag; and
a second connector for connecting to the first connector of the dispenser;
the second connector providing power to the circuit board when the second connector is connected to the first connector and for providing the signal indicative of the actuation of the dispenser to the circuit board; and
module wireless communication circuitry located on the circuit board; and
the data tag;
the data tag containing data tag wireless communication circuitry for wirelessly communicating with the compliance module.

17. The compliance monitoring system of claim 16 wherein the module wireless communication circuitry comprises one or more radio frequency transceivers.

18. The compliance monitoring system of claim 16 wherein the data tag module wireless communication circuitry comprises one or more radio frequency transceivers.

19. The compliance monitoring system of claim 16 further comprising an indicator to indicate when soap or sanitizer has been dispensed to an individual associated with the data tag.

20. The compliance monitoring system of claim 16 further comprising a refill unit including a container, a pump, and a soap or sanitizer for placement in the dispenser.

* * * * *